United States Patent [19]
Ishiguro

[11] Patent Number: 4,791,066
[45] Date of Patent: Dec. 13, 1988

[54] IMMUNOELECTROPHORESIS METHOD FOR DIAGNOSING AND DIFFERENTIATING CANCER USING LECTINS

[75] Inventor: Tatsuya Ishiguro, Kyoto, Japan

[73] Assignee: Kyowa Medex Co., Ltd., Toyota, Japan

[21] Appl. No.: 762,970

[22] Filed: Aug. 6, 1985

[30] Foreign Application Priority Data

Aug. 7, 1984 [JP] Japan .................. 59-165351

[51] Int. Cl.$^4$ .................. G01N 33/558; G01N 33/53
[52] U.S. Cl. .................. 436/516; 436/501; 436/514; 436/827; 436/813; 435/7
[58] Field of Search ........... 436/501, 514, 516, 827; 435/7

[56] References Cited

U.S. PATENT DOCUMENTS 4,329,213  6/1982  Elwing .................. 436/516
4,389,392  6/1983  Adachi .................. 436/827
4,455,380  6/1984  Adachi .................. 436/504

OTHER PUBLICATIONS

Aoyagi et al, Gann 75, 809–815: Sep. 1984.
Breborowicz et al, Scand. J. Immunol. 14, 15–20, 1981.
Kaneko et al, Tumor Res. 18 (Special Issue), S39–S47 (1983).
Chem. Abstracts 96(11), 82101c (1982), Miyazaki et al., "Lectin affinities of α-fetoprotein in liver cirrhosis; . . ."
Cancer 55(1), 156–159 (1985), Ishiguro et al., "Serum α-fetoprotein subfractions . . ."
Electrophor '83, pp. 611–618 (1984), Taketa et al., "Separation and identification of different molecular species . . ."
Chem. Abstracts 102(9), 75096Z (1985), Ishiguro et al., "α-Fetoprotein subfractions in serums . . ."
Chem. Abstracts 101(1), 4856k (1984), Taketa et al., "Molecular species of human α-fetoprotein and α--glutamyltransferase . . ."
Chem. Abstracts 95(15), 128616j (1981), Breborowicz et al., "Application of lectin affinity electrophoresis . . ."

Primary Examiner—Esther M. Kepplinger
Assistant Examiner—Stephen C. Wieder
Attorney, Agent, or Firm—Michael N. Meller

[57] ABSTRACT

Disclosed is a method for diagnosing and differentiating cancer by qualitative and quantitative determination according to an immuno-serological assay of cancer-related antigens in a body fluid, particularly glycoprotein, glycolipid and glycoantigen produced by cancerization or dedifferentiation of normal cells.

4 Claims, No Drawings

IMMUNOELECTROPHORESIS METHOD FOR DIAGNOSING AND DIFFERENTIATING CANCER USING LECTINS

BACKGROUND OF THE INVENTION

1. Field of Invention

This invention relates to a method for diagnosing cancer by qualitative and quantitative determination according to an immuno-serological assay of cancer-related antigens in a body fluid, particularly glycoprotein, glycolipid and glycoantigen produced by cancerization or dedifferentiation of normal cells.

2. Prior Art

Heretofore, specific immuno-serological assay of cancer has been carried out according to methods for assaying cancer-specific glycoprotein as a cancer-diagnosing marker. These methods utilize the immunogenicity of protein moiety of glycoprotein, where the tumor marker includes, for example, α-fetoprotein (hereinafter referred to as AFP), carcinoembryonic antigen (hereinafter referred to as CEA), γ-glutamyltranspeptidase (hereinafter referred to as γ-GTP), human chorionic gonadotropin (hereinafter referred to as HCG), etc.

For example, measurement of serum AFP value is known as a specific immunoserological diagnosis of primary hepatic carcinoma. So long as its increase is small, it is difficult to decide whether it is caused by the regeneration of hepatocyte or by hepatoma cells. AFP considerably increases not only in the case of primary hepatic carcinoma, but also sometimes in the case of metastasis to the liver from the oophoroma, or sometimes from the gastric cancer and the pancreatic cancer (metastatic hepatic carcinoma), and thus the differential diagnosis of cancer is hard to make on the basis of mere quantitative change.

SUMMARY OF THE INVENTION

Taking into account the facts that cancer-related glycoantigens produced from undifferentiation type cells (particular cancer cells) are released into the body fluid with cell cancerization; the glycoantigens have local differences in the steric structure from those produced from the normal differentiation type cells; lectin as the glycide-bound protein can specifically recognize the local steric structures of these glycoantigen, the present inventor has found that in a method for assaying the lectin bindability by affinity cross-lined immunoelectrophoresis (hereinafter referred to as ACIE), the assay accuracy can be improved by high sensitive assay using peroxidase-labelled protein A, 4-methoxy-1-naphthol and hydrogen peroxide in a coloring system after the electrophoresis (the peroxidase is hereinafter referred to as POD), and also the assay time can be shortened. Furthermore, the present inventor has found that the kind of cancer can definitely be differentiated by properly combining the binding specificities of lectins.

DETAILED DESCRIPTION

The present invention relates to a method for diagnosing cancer by assaying a bindability of lectin to a cancer-related antigen in a body fluid by ACIE, and differentiating the kind of cancer by one of or a combination of at least two of the assay results. Furthermore, the diagnosis of cancer can be carried out with a higher sensitivity by assay using POD-labelled protein A, 4-methoxy-1-naphthol and hydrogen peroxide in the coloring in the ACIE.

The body fluid to be used in the present invention is various body fluids including, for example, blood, urine, saliva, gastric juice, intestinal juice, pancreatic juice, bile, cell tissue fluid, edema fluid, ascitic fluid, hydrothorax fluid, hydropericardic fluid, synovial fluid, cerebrospinal fluid, amniotic fluid, genital secretion fluid, mother's milk, nasal mucus, phlegm, tear, sweat, etc., and it is particularly preferable to use blood in the form of serum or plasma.

The cancer-related glycoantigen includes AFP, CEA, HCG, γ-GTP, etc.

The lectin to be used in the present invention includes jack bean lectin (hereinafter referred to as ConA) and lentil lectin (hereinafter referred to as LCH) as lectins capable of being specifically bound to α-D-glucose and α-D-mannose; isolectin PHA-E of kidney bean lectin (hereinafter referred to as PHA) as lectin capable of being specifically bound to N-acetylgalactosamine; isolectin RCA-I of castor bean lectin (hereinafter referred to as RCA) as lectin capable of being specifically bound to β-D-galactose; isolectin BSA-II of banderilla bean lectin (hereinafter referred to as BSA) as lectin capable of being specifically bound to N-acetylglucosamine, etc.

In the present method, it is preferable to utilize ACIE method for separation and identification of cancer-related glycoantigens. That is, a sample containing a cancer-related glycoantigen is subjected to one-dimensional electrophoresis separation in a lectin-containing gel, and then the individual separated fractions are subjected to two-dimensional electrophoresis and coloring in an antiserum-containing gel, whereby the individual fractions can be quantitatively determined as sharp precipitate peaks. The lectin bindability can be determined from the specific change in the migration distance.

In the present invention, an enzyme immunoassay is used for the coloring after the ACIE. Particularly, a coloring system comprising POD-labelled protein A, 4-methoxy-1-naphthol and hydrogen peroxide is a clear, rapid and simple means with a high sensitivity and a high separability, which is very useful for definite diagnosis of cancer.

The diagnosis of cancer may be possible to some extent by a single bindability to lectin, but not satisfactorily, and it can be made more definitely by a combination of at least two bindabilities to lectin. The combination depends on the nature of assay substance, and, for example, ConA, LCH, etc. are used for the assay of AFP.

More particularly, AFP, a kind of embryonic protein, is a glycoprotein existing in the blood of patients suffering from primary hepatic carcinoma, gonadal teratoma, or oophoroma. By ACIE, AFP is separated into several fractions due to the difference in bindability to lectin. For example, with ConA, AFP is separated into two fractions, i.e. a ConA-bound fraction and a ConA-unbound fraction. It is ontogeneologically known that the ConA-bound AFP originates from the hepatocytes and the ConA-unbound AFP originates mostly from the vitellicle. When the serum AFP of patients suffering from the primary hepatic carcinoma is assayed in the present invention, a fraction originating partly from the vitellicle (hereinafter referred to as peak b) is found besides the AFP fraction originating mostly from the embryonic hepatocytes (hereinafter referred to as peak a). In every serum AFP of patients suffering from the metastatic hepatic carcinoma, the fraction originating from the vitellicle (peak b) is found. With LCH, the embryonic AFP is likewise separated into 4 fractions of peaks A, B, C and D. It is assayed from changes in AFP-producing sites with the elapse of time that peaks A and C are fractions originating from the hepatocytes and peaks B and D are fractions originating from the vitellicle. It is observed in the AFP fraction patterns of the primary hepatic carcinoma and metastatic hepatic carcinoma that only peaks A and C are found in every primary hepatic carcinoma, whereas in the metastatic hepatic carcinoma, peak B is found besides the peaks A and C. That is the AFP fractions produced in the embryonic hepatocytes mainly appear in the case of the primary hepatic carcinoma, whereas in the case of metastatic hepatic carcinoma, a fraction produced in the vitellicle is found besides the AFP originating from fetal liver. Thus, it is possible to make differential diagnosis between the primary hepatic carcinoma and the metastatic hepatic carcinoma with the guidance of the AFP fraction originating from the vitellicle.

Furthermore, with other lectins, i.e. PHA-E, RCA-I and BSA-II, the AFP in the amniotic fluid fails to show a specific behavior with the elapse of time, whereas AFP in the serum of cancer patients shows a specific fraction pattern.

The cancer-related glycoantigen shows a complicated steric structure, and the individual lectins partially recognize the structure. Thus, no definite diagnosis of cancer can be made from the glycospecific bindability to a single kind of lectin. By an appropriate combination of 5 kinds of lectins, i.e. ConA, LCH, PHA-E, RCA-I, and BSA-II, the steric structure of a cancer-related glycoantigen can be discriminated more definitely, and more definite differential diagnosis of cancer can be made. The amount of assay sample, the amount of lectin, the amount and proportion of POD-labelled protein A, the amount of substrate, the reaction time, the temperature and the electrophoresis condition depend on the kind of a substance to be assayed, the kind of lectin, the titer of a receptor to be used, the kind of a carrier, etc., and thus the most appropriate conditions must be experimentally determined for each assay before carrying out the present method.

Modes of carrying out the present invention will be described in detail below.

A definite amount, for example, at least 5 $\mu$l, preferably, 5 to 10 $\mu$l of a body fluid is diffused in a lectin-containing gel by one-dimensional electrophoresis. After the one-dimensional migration, each of the separated fractions is subjected to another electrophoresis in the two-dimensional direction in an antiserum-containing gel and to detection by enzyme immunoassay.

The lectin concentration depends on the kinds of a substance to be assayed and lectin, and generally the separability depends also on the concentration. The present invention provides a high sensitive assay method which is operable even at a low concentration of lectin such as 200 to 600 $\mu$g/ml.

Any gel carrier is usable without qualification. In the case of two-dimensional ACIE, it is preferable to use agarose having a particularly low electroosmosis owing to less gel deformation. The gel carrier can be prepared according to a conventional procedure. For example, a predetermined amount of agarose is added to a dilute solution such as distilled water, a barbital buffer solution at a pH of about 8.6 or a Tris-hydrochloric acid buffer solution, and heated at a temperature from 60° to 80° C. with gentle stirring, and then the solution is made to flow onto a desired flat plate, left for cooling and coagulated into a gel state.

The gel concentration is usually 0.5 to 2.0% by weight, preferably 0.8 to 1.0% by weight, and, if necessary, an antiseptic may be added thereto.

When the gel is subjected to electrophoresis for a long time, the gel surface is dried owing to the heat generation, causing a deformation. Furthermore, the binding of lectin to the glycoantigen is generally stronger at a lower temperature, and thus it is preferable to carry out the electrophoresis at a temperature of not higher than 15° C., preferably 5° to 10° C. For example, in an electronic cooling migration apparatus, efficient separation can be carried out even at a low concentration of lectin.

The longer is the one-dimensional migration distance of ACIE, the better is the separation. However, a correspondingly larger amount of lectin will be required, and a longer mignation time will be required. Thus, at least 6 cm is a sufficient migration distance. As a control marker for the electrophoresis, a coloring matter, e.g. Bromophenol Blue (hereinafter referred to as BPB)-bound albumin is made to flow in parallel with the assay sample. In the case of AFP, it is sufficient that the BPB-bound albumin can migrate up to about 6 to 7 cm.

On the other hand, the two-dimensional electrophoresis usually takes a long time such as at least 16 hours, whereas the present assay method has such a high assay sensitivity that migration for 2 to 6 hours, preferably 2 to 4 hours, is enough.

As described above, a cancer-related glycoantigen in a body fluid can be assayed advantageously by the present invention, thereby differential diagnosis of cancer is possible, and thus the present invention is clinically very useful.

The present invention will be described in detail below, referring to Examples, but the scope of the present invention will not be restricted by the following examples.

EXAMPLE 1

Differential diagnosis of hepatic carcinoma by LCH (made by Pharmacia Fine Chemicals Inc., Sweden)-ACIE (a) Preparation of assay samples Individual serum of 48 cases of primary hepatic carcinoma and 8 cases of metastatic hepatic carcinoma were diluted with normal human serum (AFP: less than 5 ng/ml) to make samples at an adjusted AFP concentration of less than 30,000 ng/ml.

(b) Preparation of LCH-containing agarose plate (for one-dimensional electrophoresis)

To 1.0% agarose (made by FMC Marine Colloids Division, U.S.A., and dissolved in a barbital buffer solution having pH 8.6 and an ionic strength of 0.05) was added 200 $\mu$g/ml LCH and mixed. Then, 15 ml of the LCH-containing agarose gel was poured into a gel bond (made by FMC Marine Colloids Division, 110×125 mm), and coagulated to make an LCH-containing agarose plate having a thickness of about 1 mm.

(c) Preparation of anti-AFP serum-containing agarose plate (for two-dimensional electrophoresis)

To 10 ml of 1.0% agarose was added 20 $\mu$l of anti-AFP serum (made by DAKO Co., Denmark). Then 10 ml of the anti-AFP serum-containing agarose gel was poured into the same gel bond as above, and coagulated to make an anti-AFP serum-containing agarose plate having a thickness of about 1 mm.

(d) Preparation of diluted POD-labelled protein A solution

To 20 μl of POD-labelled protein A (made by E.Y. Laboratories, U.S.A.) was added 10 ml of a dilute solution (prepared by dissolving 14.0 g of NaCl in 1( of barbital buffer solution having pH 8.6) to make a 0.2% POD-labelled protein A dilute solution.

(e) Preparation of coloring reagent solution

Just before application, 200 μl of 4-methoxy-1-naphthol (made by Aldrich Co., U.S.A.), 10 ml of 0.05M Tris buffer solution (a solution made by mixing 12.114 g/l trishydroxymethylaminomethane and 0.1M HCl in a ratio of 100:77, pH 7.6) and a drop of 30% $H_2O_2$ were mixed together to make a coloring reagent solution.

(f) Measurement of AFP

At first, 10 μl of the sample prepared in section (a) was poured into holes (4 mm in diameter) on the LCH-containing agarose plate prepared in section (b), and subjected to one-dimensional electrophoresis. Migration was carried out with barbital buffer solution (pH 8.6) at 3 mA/cm for 90 minutes with cooling at 10° C.

As a control, human serum albumin [fraction V, made by Sigma Co., U.S.A., containing 5 μl of 0.01% BPB] was used and the about 6 cm-migrated position was marked.

After the one-dimensional electrophoresis, the agarose plate was cut off with width of about 1 cm in parallel to the migrating direction, tightly placed on the anti-AFP-containing agarose plate prepared in section (c), and subjected to two-dimensional electrophoresis in the direction perpendicular to the direction of one-dimension development at 2.5 mA/cm for 3 hours with cooling at 10° C.

After the migration, the plate was treated with an adsorbent pad (made by Nihon Shoji Co., Japan) for 2 to 3 minutes for elimination of unbound substance, and then washed with a phosphate buffer solution (pH 7.2) for 30 minutes. Again, the plate was dried with an adsorbent pad, and 10 ml of POD-labelled protein A prepared in section (c), was poured onto the flat plate. After the reaction for 30 mintues, drying with an adsorbent pad, washing with a phosphate buffer solution (pH 7.2) for 30 minutes and drying with an adsorbent pad were repeated in the same manner as above, and then 10 ml of the coloring reagent solution prepared in section (e) was added thereto. The plate was subjected to reaction for 2 to 3 minutes. After the washing with water for 2 to 3 minutes and drying with an adsorbent pad, a distance from the albumin position obtained by the one-dimensional electrophoresis to a migration peak shown in the two-dimensional electrophoresis was measured.

As a result, typical migration patterns of serums of patients suffering from the hepatic carcinoma by LCH-ACIE are divided into (1) type in which only peak A appears alone (Type I), (2) type in which only peak C appears alone (Type II), (3) type in which two peaks, i.e. peak A and peak C appear (Type III) and (4) type in which peak B appears besides peak A or peak C (Type IV).

Type III is further divided into (a) type in which peak A is higher than peak C (Type IIIa), and (b) type in which peak C is higher than peak A (Type IIIb) according to quantitative difference.

Type IV is further divided into (a) type in which two peaks, i.e. peak A and peak B appear (Type IVa), (b) type in which three peaks, i.e. peak A, peak B and peak C appear (Type IVb), and (c) type in which only peak B appears (Type IVc).

As shown in Table 1, AFP in the serums of primary hepatic carcinoma is fractionated into Type I, Type II and Type III, whereas that of metastatic hepatic carcinoma is all fractionated into Type IV. Thus, this is useful for differentiation between the primary hepatic carcinoma and the metastatic hepatic carcinoma.

TABLE 1

| AFP fraction appearance frequency by LCH-ACIE | | | |
|---|---|---|---|
| Fraction pattern | Fraction as appeared | Primary hepatic carcinoma | Metastatic hepatic carcinoma |
| Type I | A | 2 (4.2%) | 0 0 |
| Type II | C | 6 (12.5%) | 0 0 |
| Type III | | | |
| Type IIIa | A ≧ C | 21 (43.7%) | 0 0 |
| Type IIIb | A < C | 19 (39.6%) | 0 0 |
| Type IV | | | |
| Type IVa | A B | 0 | 4 (50.0%) |
| Type IVb | A B C | 0 | 2 (25.0%) |
| Type IVc | B | 0 | 2 (25.0%) |
| | | 48 | 8 |

EXAMPLE 2

Differential diagnosis of hepatic carcinoma by ConA-ACIE

Assay was carried out for the same serum samples in the same manner as in Example 1, except that a ConA (made by Pharmacia Fine Chemicals)-containing agarose plate (ConA: 600 μg/ml) was used in place of the LCH-containing agarose plate.

As a result, typical migration patterns of serums of patients suffering from the hepatic carcinoma by ConA-ACIE are divided into (1) type in which only peak a appears (Type 1), (2) type in which two fractions of peak a and peak b appear (Type 2), and (3) type in which only peak b appears (Type 3).

As shown in Tables 2 and 3, AFP in the serum of primary hepatic carcinoma is fractionated into Type 1 (only peak a) and Type 2 (peak a > peak b), whereas that in the metastatic hepatic carcinoma is fractionated into Type 2 (peak a < peak b) and Type 3. This is useful for differentiation of the primary hepatic carcinoma and the metastatic hepatic carcinoma.

TABLE 2

| AFP fraction appearance frequency by ConA-ACIE | | | |
|---|---|---|---|
| Fraction pattern | Fraction as appeared | Primary hepatic carcinoma | Metastatic hepatic carcinoma |
| Type 1 | a | 30 (62.5%) | 0 |
| Type 2 | a b | 18* (37.5%) | 6 (75%) |
| Type 3 | b | 0 | 2 (25%) |
| | | 48 | 8 |

*At least two measurements were made for each case, and every case where Type 2 appeared in at least one measurement was classified into Type 2.

TABLE 3

Height of peak b and kind of hepatic carcinoma in Type 2 by ConA-ACIE

|  | Primary hepatic carcinoma | Metastatic hepatic carcinoma |
|---|---|---|
| Number of investigation | 18 | 6 |
| Height of peak b |  |  |
| Average % | 14.1 ± 3.6*1 | 44.5 ± 20.2*2 |
| Range | 8–12 | 17–68 |

*1 The higher value was adopted where several measurements were made for each case.
*2 The lower value was adopted where several measurements were made for each case.

EXAMPLE 3

Differential diagnosis of AFP-producing diseases by PHA-E-ACIE

Assay was carried out for the individual serums from 5 cases of primary hepatic carcinoma, 4 cases of metastatic hepatic carcinoma, 4 case of oophoroma, and one case of orchioncus in the same manner as in Example 1 except that a PHA-E (made by E.Y. Laboratories, U.S.A.)-containing agarose plate (PHA-E: 200 μg/ml) was used in place of the LCH-containing agarose plate. Migration peaks were named 4 fractions of peak A, peak B, peak C and peak D on the ground of migration distances shown in Table 4.

TABLE 4

Classification of individual peaks by migration distances

| Peak A | Peak B | Peak C | Peak D |
|---|---|---|---|
| 21.0< | 16.0–21.0 | 12.0–16.0 | 12.0 > |

(unit mm)

As a result, the migration patterns of serums of patients suffering from various cancers by PHA-E-ACIE are divided into (1) type in which only peak C, only peak D, or two fractions of peak C and peak D appear (Type 1), and (2) type in which two fractions of peak A and peak C, only peak B, two fractions of peak B and peak C; or three fractions of peak B, peak C and peak D appear (Type 2). Type 2 is characterized by appearance of either peak A or peak B (shown as underlined in Table 5).

No specific change between the AFP in amniotic fluid and the pregnancy period was observed in PHA-E-ACIE. However, general tendency was observed with the serums of cancer patients, as shown in Table 5.

TABLE 5

| | | AFP fraction appearance frequency by PHA-E-ACIE | | | |
|---|---|---|---|---|---|
| Fraction pattern | Appearance frequency | Primary hepatic carcinoma | Metastatic hepatic carcinoma | Oophoroma | Orchioncus |
| Type 1 | C, D, CD | 5 | 0 | 1 | 0 |
| Type 2 | AC, B, BC, BCD | 0 | 4 | 3 | 1 |
| | | 5 | 4 | 4 | 1 |

EXAMPLE 4

Differential diagnosis of AFP-producing diseases by RCA-I-ACIE

Assay was carried out for the same serum samples as in Example 3 in the same manner as in Example 1, except that an RCA-I (made by E.Y. Laboratories)-containing agarose plate (RCA-I: 200 μg/ml) was used in place of the LCH-containing agarose plate.

Migration peaks were named 4 fractions of peak A, peak B, peak C and peak D on the ground of migration distances shown in Table 4.

As a result, the migration patterns of serums from patients suffering from various cancers by RCA-I-ACIE were divided into (1) type in which only peak C, only peak D, or two fractions of peak C and peak D appear (Type 1); (2) two fractions of peak A and peak C, two fractions of peak A and peak D, or three fractions of peak A, peak C and peak D appear (Type 2); and (3) type in which three fractions of peak A, peak B and peak D, or two fractions of peak B and peak D appear (Type 3). Type 2 and type 3 are characterized by appearance of peak A and/or peak B (shown as underlined in Table 6).

No specific change in the AFP in amniotic fluid and the pregnancy period was observed in RCA-I-ACIE. However, general tendency was observed in the serums of cancer patients as shown in Table 6.

TABLE 6

| | | AFD fraction appearance frequency by RCA-I-ACIE | | | |
|---|---|---|---|---|---|
| Fraction pattern | Appearance frequency | Primary hepatic carcinoma | Metastatic hepatic carcinoma | Oophoroma | Orchioncus |
| Type 1 | C, D, CD | 5 | 1 | 0 | 0 |
| Type 2 | AC, AD, ACD | 0 | 2 | 3 | 1 |
| Type 3 | ABD, BD | 0 | 1 | 1 | 0 |
| | | 5 | 4 | 4 | 1 |

EXAMPLE 5

Differential diagnosis of AFP-producing diseases by BSA-II-ACIE

Assay was carried out for the same serum samples as in Example 3 in the same manner as in Example 1 except that a BSA-II (made by E.Y. Laboratories)-containing agarose plate (BSA-II: 200 μg/ml) was used in place of the LCH-containing agarose plate.

Migration peaks were named 4 fractions of peak A, peak B, peak C and peak D on the ground of migration distances shown in Table 4.

As a result, the migration patterns of serums from patients suffering from various cancers by BSA-II-ACIE were divided into (1) type in which only peak C or only peak D appears (Type 1), and (2) type in which three fractions of peak A, peak B and peak D, or two fractions of peak B and peak D appear (Type 2). Type 2 is characterized by appearance of peak A and/or peak B (shown as underlined in Table 7).

No specific change between the AFP in amniotic fluid and the pregnancy period was observed in BSA-II-ACIE. However, general tendency was observed in the serums of cancer

TABLE 7

| | AFP fraction appearance frequency by BSA-II-ACIE | | | | |
|---|---|---|---|---|---|
| Fraction pattern | Appearance frequency | Primary hepatic carcinoma | Metastatic hepatic carcinoma | Oophoroma | Orchioncus |
| Type 1 | C, D | 5 | 1 | 4 | 1 |
| Type 2 | ABD, BD | 0 | 3 | 0 | 0 |
| | | 5 | 4 | 4 | 1 |

EXAMPLE 6

Differential diagnosis of cancer by combination of ConA and LCH:

Cases of obscure differentiation in Example 2, that is, 4 cases showing a high peak b value (14% or higher) in the primary hepatic carcinoma and 6 cases showing a low peak b value (45% or lower) in the metastatic hepatic cancer in the patient serums classified into type 2 by ConA were checked by the results of fraction patterns by LCH (Example 1).

As a result, it was found that all the primary hepatic carcinoma belonged to type III, and that all the metastatic hepatic carcinoma belonged to Type IV.

EXAMPLE 7

Differential diagnosis of cancer by combination of ConA and PHA-E:

Among the cases of obscure differentiation in Example 2, that is, cases showing a high peak b value (14% or higher) in the primary hepatic cancer and cases showing a low peak b value (45% or lower) in the metastatic hepatic carcinoma in the patient serums belonging to type 2 by ConA, a few cases of the patient serums were investigated by PHA-E and the fraction patterns were estimated compared with the results of Example 3.

As a result, it was found that all the primary hepatic carcinoma belonged to Type 1, and that all the metastatic hepatic carcinoma belonged to Type 2.

EXAMPLE 8

Differential diagnosis of cancer by combination of PHA-E and RCA-I:

Cases of obscure differentiation in Examples 3 and 4, that is, the serums of patients suffering from the oophoroma showing Type 1 by PHA-E were classified into Type 3 by RCA-I.

The serums of patients suffering from the metastatic hepatic carcinoma showing Type 1 by RCA-I were classified into Type 2 by RHA-E.

EXAMPLE 9

Differential diagnosis of cancer by combination of PHA-E and BSA-II:

Cases of obscure differentiation in Examples 3 and 5, that is, serums of patients suffering from the oophoroma showing Type 1 by PHA-E were classified into Type 1 by BSA-II.

The serums of patients suffering from the metastatic hepatic carcinoma showing Type 1 by BSA-II were classified into Type 2 by PHA-E.

EXAMPLE 10

Differential diagnosis of cancer by combination of RCA-I and LCH:

Cases of obscure differentiation in Example 4, that is, serums of patient suffering from the metastatic hepatic carcinoma showing Type 1 by RCA-I were classified into Type IVb by LCH (Example 2).

EXAMPLE 11

Differential diagnosis of cancer by combination of RCA-I and BSA-II

Cases of obscure differentiation in Examples 4 and 5, that is, serums of patients suffering from the metastatic hepatic cancer showing Type 1 by RCA-I were classified into Type 2 by BSA-II.

Furthermore, the serums of patients suffering from the metastatic hepatic carcinoma showing Type 1 by BSA-II were classified into Type 3 by RCA-I.

EXAMPLE 12

Differential diagnosis of cancer by combination of BSA-II and LCH

Cases of obscure differentiation in Example 5, that is, serums of patients suffering from the metastatic hepatic carcinoma showing Type 1 by BSA-II were classified into Type IVb by LCH (Example 2).

As described above, it is possible to make more definite differential diagnosis of cancer by combining 5 kinds of lectins, i.e. ConA, LCH, PHA-E, RCA-I and BSA-II complementarily as desired.

What is claimed is:

1. A method of differentiating primary hepatic carcinoma from metastatic hepatic carcinoma, comprising obtaining a sample of a body fluid from a patient suspected of having hepatic carcinoma, assaying said sample by means of cross-immunoaffinoelectrophoresis on each one of a pair of lectins selected from the group consisting of ConA-LCH, ConA-PHA-E, RCA-I-LCH, RCA-I-BSA-II and BSA-II-LCH, for the presence of α-fetoprotein specific fraction binding patterns; and differentiating primary hepatic carcinoma from metastatic hepatic carcinoma based on the resulting specific fraction binding patterns.

2. The method according to claim 1, wherein coloring after the cross-immunoaffinoelectrophoresis is carried out by a highly sensitive assay using peroxidase-labelled protein A, 4-methoxy-1-naphtol and hydrogen peroxide.

3. A method of differentiating oophoroma from metastatic hepatic carcinoma, comprising obtaining a sample of a body fluid from a patient suspected of having oophoroma or metastatic hepatic carcinoma, assaying said sample by means of crossed-immunoaffinoelectrophoresis on each one of a pair of lectins selected form the group consisting of PHA-E-RCA-I and PHA-E-BSA-II, for the presence of α-fetoprotein specific fraction binding patterns; and differentiating oophoroma from metastatic hepatic carcinoma based on the resulting specific fraction binding patterns.

4. The method according to claim 3 wherein coloring after the cross-immunoaffinoelectrophoresis is carried out by a highly sensitive assay using peroxidase-labelled protein A, 4-methoxy-1-naphthol and hydrogen peroxide.

* * * * *